(12) United States Patent
Yoshikawa (10) Patent No.: US 9,510,996 B2
(45) Date of Patent: Dec. 6, 2016

(54) MULTI-LAYER TUBE FOR MEDICAL USE AND MEDICAL INFUSION BAG

(75) Inventor: Katsuyuki Yoshikawa, Tokyo (JP)

(73) Assignee: Hosokawa Yoko Co., Ltd., Tokyo (JP)

( * ) Notice: Subject to any disclaimer, the term of this patent is extended or adjusted under 35 U.S.C. 154(b) by 29 days.

(21) Appl. No.: 13/813,156

(22) PCT Filed: Jul. 27, 2011

(86) PCT No.: PCT/JP2011/067073
§ 371 (c)(1),
(2), (4) Date: Jan. 29, 2013

(87) PCT Pub. No.: WO2012/014927
PCT Pub. Date: Feb. 2, 2012

(65) Prior Publication Data
US 2013/0123739 A1    May 16, 2013

(30) Foreign Application Priority Data

Jul. 30, 2010  (JP) .................. 2010-172263

(51) Int. Cl.
  *A61J 1/14*  (2006.01)
  *A61J 1/10*  (2006.01)
  (Continued)

(52) U.S. Cl.
  CPC .................. *A61J 1/1475* (2013.01); *A61J 1/10* (2013.01); *A61L 29/085* (2013.01); *A61M 5/14* (2013.01); *B32B 1/08* (2013.01); *B32B 7/12* (2013.01); *B32B 27/08* (2013.01); *B32B 27/32* (2013.01); *A61J 1/1468* (2015.05); *A61L 2420/08* (2013.01); *A61M 39/12* (2013.01); *B32B 2250/24* (2013.01); *B32B 2250/242* (2013.01); *B32B 2535/00* (2013.01)

(58) Field of Classification Search
  CPC ...................................................... A61J 1/1475
  See application file for complete search history.

(56) References Cited

U.S. PATENT DOCUMENTS 6,004,636 A  12/1999  Nicola et al.
6,713,137 B1  3/2004  Andersson et al.
(Continued)

FOREIGN PATENT DOCUMENTS

CN  1486243 A  3/2004
EP  0 567 210  10/1993
(Continued)

OTHER PUBLICATIONS

International Search Report in Application No. PCT/JP2011/067073, mailed Sep. 6, 2011.
(Continued)

*Primary Examiner* — Philip R Wiest
*Assistant Examiner* — Kai Weng
(74) *Attorney, Agent, or Firm* — Nixon Peabody LLP; Khaled Shami (57) ABSTRACT

Disclosed is a multi-layer tube for medical use, the tube being characterized by having: an outer layer including a resin material that contains high-density polyethylene, and an inner layer including a resin material that contains random polypropylene and/or block polypropylene. Also disclosed a medical infusion bag provided with the multi-layer tube.

3 Claims, 2 Drawing Sheets

(51) Int. Cl.
- *A61M 5/14* (2006.01)
- *A61L 29/08* (2006.01)
- *B32B 27/08* (2006.01)
- *B32B 27/32* (2006.01)
- *B32B 1/08* (2006.01)
- *B32B 7/12* (2006.01)
- *A61M 39/12* (2006.01)

(56) References Cited

U.S. PATENT DOCUMENTS

| | | | |
|---|---|---|---|
| 6,869,653 B2* | 3/2005 | Ling et al. | 428/36.9 |
| 2007/0204929 A1* | 9/2007 | Jarvenkyla | 138/145 |
| 2009/0101224 A1* | 4/2009 | Ziu | B29C 57/04 138/109 |
| 2010/0137838 A1* | 6/2010 | Hwang | B32B 27/32 604/533 |
| 2010/0163446 A1 | 7/2010 | Suzuki et al. | |

FOREIGN PATENT DOCUMENTS

| | | |
|---|---|---|
| JP | 2001-269403 A | 10/2001 |
| JP | 2004-223910 A | 8/2004 |
| JP | 3689486 B | 8/2005 |
| JP | 2007-236782 A | 9/2007 |
| JP | 4249817 B2 | 1/2009 |
| JP | 2009-154332 | 7/2009 |
| JP | 2010-523258 A | 7/2010 |
| RU | 2 183 446 | 6/2002 |
| WO | 02/055298 | 7/2002 |
| WO | 02/078952 A1 | 10/2002 |

OTHER PUBLICATIONS

Office Action in Russian Application No. 2013103481, mailed Mar. 27, 2014.

Office Action in Chinese Application No. 201180036794.1, mailed May 12, 2014 (translation of search report only).

Extended European search report for European Application No. 11812516.0, dated Dec. 17, 2013.

Database WPI, Week 200948, Thomson Scientific, London, GB; AN 2009-L48349, XP002717575.

Notice of Allowance in Russian Application No. 2013103481, mailed Jan. 28, 2015.

* cited by examiner

MULTI-LAYER TUBE FOR MEDICAL USE AND MEDICAL INFUSION BAG

TECHNICAL FIELD

The present invention relates to a multi-layer tube for medical use, which is suitably used as a tube port of a medical infusion bag, and the medical infusion bag.

This application claims priority to and the benefit of Japanese Patent Application No. 2010-172263 filed on Jul. 30, 2010, the disclosure of which is incorporated herein by reference.

BACKGROUND ART

Conventionally, a medical device such as an infusion bag or a tube port is generally manufactured using soft polyvinyl chloride containing a plasticizer. The soft polyvinyl chloride has excellent flexibility, heat resistance, strength, or the like, as well as high kink stability or a tube.

Since the soft polyvinyl chloride has a chlorine atom in a main chain, a problem of easily generating dioxin during discarding and incinerating the soft polyvinyl chloride has been encountered. Also, a butyric acid ester-based plasticizer such as dioctyl butyrate to be added for the purpose of softening may be occasionally eluted into a medical infusion, in turn seriously becoming an environmental hormone.

In recent years, a medical device using polypropylene as a main substance, instead of such soft polyvinyl chloride, has been developed.

Although polypropylene has excellent heat resistance, polypropylene has a high possibility of being brittle in a low temperature environment. Thus, when a medical infusion bag made of polypropylene is used in a low temperature environment, it encounters a problem due to poor cold resistance of polypropylene such as tearing of the bag or the like. Further, polypropylene is often provided with an additive such as an antioxidant in order to prevent deterioration. For this reason, even in a case of using polypropylene, as with the case of using soft polyvinyl chloride, the additive into a medical infusion may be eluted.

As a substance to be used instead of polypropylene, polyethylene has been attracting attention. Polyethylene shows favorable cold resistance and may reduce the amount of additive required to be added polyethylene. Therefore, components eluted into a medical infusion are decreased. In addition, since polyethylene is inexpensive, it is possible to reduce production costs.

However, polyethylene typically has a heat resistant temperature of about 110° C., thus showing relatively lower heat resistance than polypropylene. For instance, for a medical infusion bag, since a medical infusion is disinfected (that is, sterilized) at a high temperature of 121° C. after filling the bag with the medical infusion, it requires improvement of heat resistance of polyethylene in order to manufacture the bag using polyethylene.

Polyethylene capable of withstanding high pressure steam sterilization at 121° C. has been recently developed and attracted attention as a medical infusion bag material.

When filling the medical infusion bag with the medical infusion, in general, a body of the bag storing the medical infusion therein has a tube, a so-called tube port, welded thereto and the medical infusion is fed into the bag body through the tube.

After feeding the medical infusion, a connector such as a twist-off spike port which is fluid-tight using a membrane is introduced into a front end of the tube, the tube is closed using a cap, and then high pressure steam sterilization is performed. Further, dripping is generally performed by piercing the connector with a needle mounted on the front end of a medical infusion line.

Accordingly, since the high pressure steam sterilization is executed while the tube is welded on the body of the medical infusion bag, the tube also requires excellent heat resistance. In addition, a contact part between the bag body and the tube, a contact part between the tube and the connector, or the like should be closely, that is, fluid-tightly, adhered.

With respect to the tube, for example, Patent Document 1 discloses a medical tube provided with three layers, including an outer layer made of soft polyvinyl chloride or a polyurethane-based copolymer as a main component, an intermediate layer made of chlorinated polyethylene or a maleic acid-based copolymer as a main component, and an inner layer made of polyethylene or ethylene and an α-olefin copolymer as a main component.

Further, Patent Document 2 discloses a multi-layer tube including an outer layer, an intermediate layer and an inner layer. In particular, the multi-layer tube is described to have the inner or outer layer which includes a composition of 85% of a three-component mixture containing polypropylene, a copolymer of ethylene and acrylic acid ester and a styrene-ethylene-butylene-styrene block copolymer, and 15% of a copolymer of ethylene and propylene.

PRIOR ART

Patent Document

[Patent Document 1]: Japanese Unexamined Patent Application, First Publication No. 2001-269403
[Patent Document 2]: Japanese Patent No. 3689486

SUMMARY OF THE INVENTION

Problems to be Solved by the Invention

The medical tube described in Patent Document 1 has insufficient adhesiveness for a polyethylene bag.

Patent Document 2 does not specifically describe provision of tolerance to high pressure steam sterilization at 121° C., and the multi-layer tube described in Patent Document 2 does not have sufficient heat resistance with respect to high pressure steam sterilization at 121° C.

As described above, in the past, polypropylene is now mainly used as a material of a medical infusion bag replacing soft polyvinyl chloride, and thus, a tube is also made of a polypropylene-based resin. The reason for this is that the medical infusion bag can be easily adhered with the tube by heat sealing if the tube is formed of the same polypropylene-based resin as the bag. For the above reason, even with respect to members associated with a non-vinyl chloride-based medical infusion bag, connectors joined to the tube such as a twist-off spike port and the like are also used based on the assumption that these are connected to a tube made of polypropylene, and mostly prepared using polypropylene.

Accordingly, the tube combined with a polyethylene bag capable of withstanding high pressure steam sterilization at 121° C. needs adhesiveness to a medical device formed of a material different from that of the tube as well as excellent heat resistance. That is, the tube also requires adhesiveness to both of a polyethylene bag and a connector made of polypropylene.

In consideration of the above-mentioned circumstances, it is an object of the present invention to provide a multi-layer tube for medical use having excellent adhesiveness to both of a polyethylene bag and a connector as well as heat resistance, and a medical infusion bag including the above multi-layer tube for medical use.

Means for Solving the Problems

The multi-layer tube for medical use of the present invention includes an outer layer including a resin material that contains high-density polyethylene, and an inner layer including a resin material that contains random polypropylene and/or block polypropylene.

Also, an adhesive layer including an adhesive resin may be provided between the outer layer and the inner layer. Further, the outer layer may include a resin material that contains high-density polyethylene and an adhesive resin.

In addition, the medical infusion bag for medical use of the present invention includes a bag body formed in a bag shape using a polyethylene film, which stores a medical infusion, and a tube port welded to a bottom of the bag body, through which the medical infusion is discharged from the bag body, wherein the multi-layer tube for medical use of the present invention is used as the tube port.

Effect of the Invention

According to the present invention, it is possible to provide a multi-layer tube for medical use that has excellent adhesiveness to both of a polyethylene bag and a connector as well as heat resistance, and a medical infusion bag for medical use including the multi-layer tube for medical use.

EMBODIMENTS OF THE INVENTION

Multi-Layer Tube for Medical Use

Figure 1:
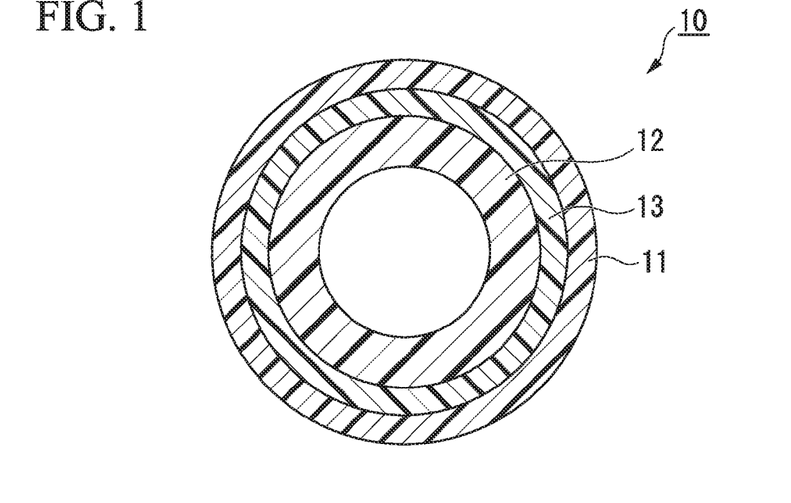
FIG. 1 is a cross-sectional view illustrating an embodiment of a multi-layer tube for medical use of the present invention.

FIG. 1 illustrates an embodiment of a multi-layer tube for medical use according to the present invention. Hereinafter, the multi-layer tube for medical use may be referred to as merely a 'tube' in this detailed description. The tube 10 may include an outer layer 11, an inner layer 12 and an adhesive layer 13 provided between the two layers. Also, referring to FIG. 1, the dimensions of the drawings are different from the actual dimensions for convenient explanation.
<Outer Layer>
The outer layer 11 is a layer contacting a polyethylene bag, that is, a bag body to be described below, and includes a resin material containing high-density polyethylene. Hereinafter, the resin material is referred to as a 'resin material for the outer layer.'

Since the outer layer 11 includes the resin material for the outer layer that contains high-density polyethylene, a tube with heat resistance capable of withstanding even in high pressure steam sterilization at 121° C. is obtained. Since a polyethylene bag and the outer layer 11 contacting the polyethylene bag include the same ethylene-based material, the outer layer is easily deposited on the polyethylene bag, in turn obtaining a tube with excellent adhesive properties.

According to the present invention, 'high-density polyethylene' means polyethylene having a density of 0.945 g/cm$^3$ or more. When the density is 0.945 g/cm$^3$ or more, a tube having excellent heat resistance is obtained. The density of polyethylene is measured based on a JIS K 7112 D method.

Preferably, the high-density polyethylene used herein is high-density polyethylene having a molecular weight distribution Mw/Mn of 6 or less. If the molecular weight distribution Mw/Mn is 6 or less, whitening of the outer layer 11 may be inhibited when a tube is fabricated by extrusion molding, and transparency of the tube may be favorably maintained. The molecular weight distribution Mw/Mn is measured by gel permeation chromatography and means a ratio of mass average molecular weight Mw to number average molecular weight Mn, which is calculated according to a calibration curve using polystyrene as a standard sample.

Although the outer layer 11 may be prepared using high-density polyethylene alone, it may also be formed using the resin material for the outer layer that contains an adhesive resin. By using the resin material for the outer layer that contains the adhesive resin, the adhesive layer 13 to be described below may be omitted and a tube including only the outer layer 11 and the inner 12 layer can be obtained.

In addition, when the adhesive resin is added to the resin material for the outer layer, the resin material for the outer layer may be prepared by pellet blending the high-density polyethylene and the adhesive resin. However, when the mixing is insufficiently conducted in a molding machine, the above two materials may be preliminarily molten and mixed by, for example, an extruder, The adhesive resin may include, for example: an elastomer such as a polyethylene-based elastomer, a styrene-based elastomer, or the like; a maleic acid anhydride-modified polyolefin such as maleic acid anhydride-modified polyethylene, maleic acid anhydride-modified polypropylene, or the like; an acrylic acid-modified polyolefin such as acrylic acid-modified polyethylene, acrylic acid-modified polypropylene, or the like; an olefin-based copolymer such as a copolymer of maleic acid anhydride and olefin, a copolymer of acrylic acid derivatives and olefin, or the like; a block copolymer having ethylene chains at both ends thereof (a material compatible with polyethylene and polypropylene), and so forth. Further, the adhesive resin may include a mixture of the above resins, and a combination of the above resins with polyethylene or polypropylene.

Among these resins, in view of excellent molding stability and suitability in medical use, the elastomer, a mixture of the elastomers, a mixture of the elastomer with polyethylene or polypropylene, and the block copolymer having ethylene chains at both ends thereof are preferably used.

When the adhesive resin is added to the resin material for outer layer, it is preferable that a content of the adhesive resin be 80 mass % or less, and more preferably, 60 mass % or less with respect to 100 mass % of the resin material for outer layer. When the content of the adhesive resin exceeds 80 mass %, a ratio of the high-density polyethylene is decreased and heat resistance of the tube may be easily reduced.

A lower limit value of the content of the adhesive resin is not particularly limited, but preferably the content is 20 mass % or more.

Preferably, the thickness of the outer layer 11 is 50 μm or less, more preferably, 20 μm or less, and most preferably, 10 μm or less. If the thickness of the outer layer 11 is 50 μm or less, flexibility of the whole tube 10 can be favorably maintained. In particular, if the thickness of the outer layer 11 is 20 μm or less, transparency of the tube 10 is further improved. When the thickness of the outer layer 11 is 10 μm or less, a tube having more excellent flexibility and transparency than a conventional tube made of polypropylene can be obtained. A lower limit value of the thickness of the outer layer 11 is not particularly limited, but preferably the content is 3 μm or more.

<Inner Layer>

The inner layer 12 is a main layer having the largest thickness in a multi-layer tube and contacting a connector that is inserted into a tube such as a twist-off spike port and connected thereto. When the tube has a double-layer structure, the inner layer means a layer other than the outer layer of the tube, while when the tube has a three-layer structure, the inner layer means a layer other than the outer layer and the adhesive layer of the tube. The inner layer 12 includes a resin material including random polypropylene and/or block polypropylene. Hereinafter, the resin material is referred to as a 'resin material for the inner layer.'

Since the inner layer 12 includes the resin material for the inner layer that contains random polypropylene and/or block polypropylene, a connector made of polypropylene and the inner layer 12 contacting the connector include the same propylene-based material, a tube with excellent adhesiveness to the connector made of polypropylene is obtained.

The random polypropylene is a random copolymer of propylene and ethylene.

Preferably, the random polypropylene used herein is random polypropylene having ethylene content of 3 mass % or more, and more preferably, random polypropylene having ethylene content of 6 mass % or more. If the ethylene content is less than 3 mass %, adhesion between the tube and the connector may be reduced and the tube loses flexibility, thus causing a problem of hardening. An upper limit value of the ethylene content is not particularly limited, but preferably the content is 9 mass % or less.

The block polypropylene may be prepared by blending propylene and an elastomer component including ethylene and/or another olefin. Preferably, the blending is executed by a reactor blending method. The block polypropylene may be prepared, for example, by adding ethylene and/or another olefin during homo-polymerization of propylene and then copolymerizing the added materials and propylene.

The other olefin may include, for example, 1-butene, 1-pentene, 4-methyl-1-pentene, 1-hexene or 1-octene, or the like.

Preferably, the block polypropylene used herein is block polypropylene having a content of an elastomer component of 15 mass % or more, and more preferably, block polypropylene having a content of an elastomer component of 40 mass % or more. When the content of an elastomer component is less than 15 mass %, adhesion between the tube and the connector is reduced and the tube loses flexibility, thus causing a problem of hardening. An upper limit value of the content of an elastomer component is not particularly limited, but preferably the content is 70 mass % or less.

Since the block polypropylene has better flexibility than random polypropylene, it shows an excellent adhesive property. Therefore, when the tube 10 includes the outer layer 11 and inner layer 12, it is preferable that the inner layer 12 be formed using block polypropylene. If the inner layer 12 is formed using the block polypropylene, a tube 10 having favorable adhesiveness to the outer layer 11 is obtained.

In addition, the random polypropylene shows less elution of components into a medical infusion than the block polypropylene. Accordingly, if the inner layer 12 is formed using the random polypropylene, a tube 10 having excellent chemical-resistance and further excellent safety is obtained.

To make the inner layer 12 flexible, resin materials for the inner layer may include, for example, a styrene-based elastomer such as a hydrogenated styrene-butadiene-elastomer, or the like, an olefin-based elastomer such as an ethylene-butene copolymer, or the like, which are used alone or as a blend by combining two or more thereof.

The inner layer 12 may have a mono-layer structure of a single layer or a multi-layer structure of multiple layers.

When the inner layer 12 has a multi-layer structure, it is preferable to adopt a construction in which at least one layer including the above-mentioned resin material for the inner layer is disposed at the outer layer 11 side, while a layer including polypropylene different from the above resin material layer is provided at a liquid contact side, that is, becomes the innermost side.

In addition, the polypropylene forming a layer on the liquid contact side of the inner layer 12 can have the following construction according to purposes thereof.

If chemical resistance is emphasized, random polypropylene without an elastomer component or homo-polypropylene as a homopolymer of propylene is preferably used in view of further inhibiting elution into a medical infusion. As the random propylene, random polypropylene having an ethylene content of 3 mass % or more is preferably used.

When adhesiveness to the connector is emphasized, polypropylene containing an elastomer component is preferably used. The polypropylene containing an elastomer component may include, for example, block polypropylene, a mixture of block polypropylene and an elastomer component, and a mixture of a random propylene and an elastomer component. The elastomer component may include, for example, a polyolefin-based elastomer, a styrene-based elastomer, and a mixture of the elastomers, or the like. In particular, the mixture of block polypropylene and the elastomer component is preferably used since it has excellent adhesiveness to a connector made of polycarbonate as well as a connector made of polypropylene.

When the tube 10 includes the outer layer 11 and the inner layer 12, it is preferable that a layer of the inner layer 12 contacting the outer layer 11 be formed using block polypropylene as described above.

Preferably, a thickness of the inner layer 12 ranges from 0.35 to 9 mm, and more preferably, 0.6 to 5 mm. If the thickness of the inner layer 12 is 0.35 mm or more, strength of the tube can be favorably maintained. On the other hand, when the thickness of the inner layer 12 is 9 mm or less, flexibility of the tube can be favorably maintained.

If the inner layer 12 has a multi-layer structure, a thickness of the layer on the liquid contact side thereof preferably ranges from 3 to 50 μm, more preferably, 3 to 20 μm, and further more preferably, 3 to 10 μm.

When the layer on the liquid contact side includes random polypropylene or homo-polypropylene, if a thickness of the layer is 50 μm or less, flexibility of the whole tube 10 can be favorably maintained. Particularly, if the thickness of the layer on the liquid contact side is 20 μm or less, flexibility of the whole tube 10 is further improved. If the thickness of the layer on the liquid contact side is 10 μm or less, flexibility of the whole tube 10 can be enhanced to such an extent as of a tube having no layer on the liquid contact side.

When the layer on the liquid contact side is polypropylene containing an elastomer component, if a thickness of the above layer is 50 μm or less, chemical resistance of the whole tube 10 is not significantly lost. In particular, if the thickness of the layer on the liquid contact side is 20 μm or less, chemical resistance of the whole tube 10 is not almost lost. Moreover, when the thickness of the layer on the liquid contact side is 10 μm, chemical resistance of the whole tube 10 may be almost the same as that of a tube having no layer on the liquid contact side.

<Adhesive Layer>

The adhesive layer 13 is a layer provided between the outer layer 11 and the inner layer 12 and has a function of bonding these two layers.

The adhesive layer 13 includes an adhesive resin. The adhesive resin forming the adhesive layer 13 may include the adhesive resin previously given as an example in the description for the outer layer 11. Among these, in view of flexibility of the whole tube 10 or excellent adhesiveness to the outer layer 11 and inner layer 12, and increased peel strength, a mixture of polypropylene and an elastomer, a mixture of block polypropylene and an elastomer, maleic acid anhydride-modified polypropylene, and a block copolymer having ethylene chains at both ends thereof, are preferably used.

Preferably, the thickness of the adhesive layer 13 ranges from 3 to 100 μm, and more preferably, 5 to 50 μm. If the thickness of the adhesive layer 13 is 3 μm or more, it is possible to uniformly adhere the outer layer 11 to the inner layer 12. In particular, if the thickness of the adhesive layer 13 is 5 μm or more, adhesion is further made uniform to reduce deviation in peel strength. On the other hand, if the thickness of the adhesive layer 13 is 100 μm or less, chemical resistance of the whole tube 10 is not significantly lost. In particular, if the thickness of the adhesive layer 13 is 50 μm or less, chemical resistance of the whole tube 10 is almost not lost.

<Fabrication Method of Tube>

In the tube of the present invention, it is preferable that the layers described above are adhered by co-extrusion.

In addition, "co-extrusion method" means that a plurality of resin materials is simultaneously extruded by multiple extruders to laminate a plurality of molten resin layers in a tube shape inside or outside of a die. Specifically, the resin material for the outer layer, the resin for the inner layer, and optionally, the adhesive resin for forming the adhesive layer are extruded at the same time and laminated in a tube shape, thereby providing a tube having an outer layer and inner layer.

An outer diameter of the tube obtained by the above method may range from about 1.1 to about 20 mm. Preferably, the thickness of the tube wall ranges from 5 to 45% of the outer diameter thereof. If the thickness of the tube wall is less than 5% of the outer diameter of the tube, it is difficult for the tube to maintain a hollow shape, and the tube is sometimes crushed and blocked. On the other hand, when the thickness of the tube wall exceeds 45% of the outer diameter thereof, the tube becomes stiff and does not easily maintain flexibility.

The tube of the present invention includes the above-mentioned outer layer and inner layer. The outer layer includes the resin material for the outer layer containing high-density polyethylene. Accordingly, the tube of the present invention has heat resistance capable of withstanding high pressure steam sterilization at 121° C.

The outer layer includes the same ethylene-based material as the polyethylene bag, while the inner layer includes the same propylene material as a connector made of polypropylene. Therefore, the tube of the present invention has excellent adhesiveness to both of the polyethylene bag and the connector, which are made of different materials.

[Medical Infusion Bag]

Figure 2:
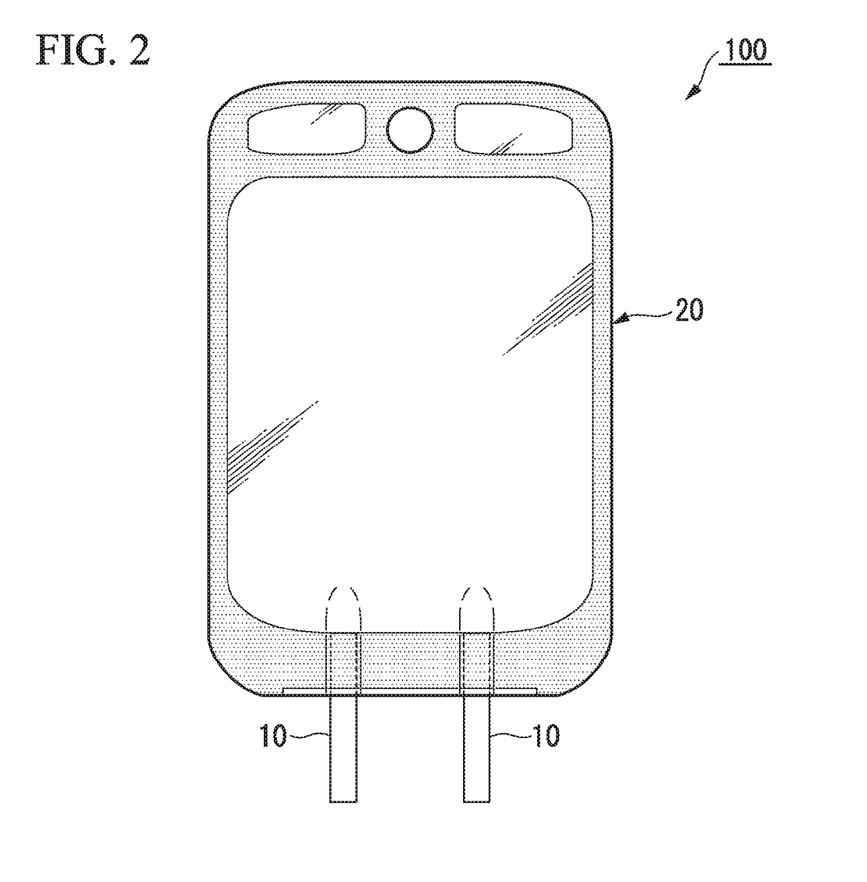
FIG. 2 is a front view illustrating an embodiment of a medical infusion bag for medical use of the present invention.

FIG. 2 illustrates an embodiment of the medical infusion bag according to the present invention. In this description, the medical infusion bag may occasionally be referred to as merely an "infusion bag."

The infusion bag 100 includes a bag body 20 storing a medical infusion and the tube 10 of the present invention welded to the bottom of the bag body 20.

The bag body 20 is a polyethylene bag formed in a bag shape using a polyethylene film.

When the polyethylene film is a multi-layer type, it may have, for example, a structure in which at least an inner layer of the bag body 20 is made of polyethylene. In particular, the polyethylene film may be a polyethylene film with a multi-layer structure in which an inner layer contains high-density polyethylene. More particularly, a polyethylene film having a multi-layer structure, in which all layers include polyethylene, may include, for example, a three-layer structure polyethylene film including an inner layer, an intermediate layer and an outer layer. Specifically, the three-layer structure polyethylene film may include, for example: a three-layer film that includes an inner layer and an outer layer, which include high-density polyethylene, and an intermediate layer including linear low-density polyethylene; a three-layer film that includes an outer layer including a mixture of low-density polyethylene and high-density polyethylene, an intermediate layer including a mixture of linear low-density polyethylene and high-density polyethylene, and an inner layer including high-density polyethylene; or the like.

The high-density polyethylene may include, for example, polyethylene having a density of 0.945 g/cm$^3$ or more. The linear low-density polyethylene may include, for example, polyethylene having a density of less than 0.945 g/cm$^3$. The low-density polyethylene may include, for example, polyethylene having a density of 0.910 to 0.930 g/cm$^3$. The density of polyethylene is measured based on a JIS K 7112 D method.

The bag body 20 is obtained by, for example, a water cooling or air cooling co-extrusion type multi-layer inflation method or a multi-layer hollow molding method, in order to form the polyethylene film in a back shape. Alternatively, the bag body may also be obtained by preparing a laminate film or laminate sheet by a co-extrusion multi-layer T die method, a dry lamination method, an extrusion lamination method, or the like, and then, processing the prepared one in a back shape through heat sealing.

The infusion bag 100 of the present invention uses the tube 10 of the present invention as a tube port. A method of welding the tube 10 to the bag body 20 is not particularly limited, however, may be conducted by, for example, inserting the tube 10 into the bottom of the bag body 20 and heat sealing a contact part therebetween.

For the infusion bag 100 of the present invention, since the outer layer of the tube 10 and the bag body 20 include the same ethylene-based material, that is, polyethylene, the tube 10 and the bag body 20 can firmly adhere to each other.

In addition, with respect to adhesion between the tube 10 and the bag body 20, if the peel strength at the welded part is 10 N/15 mm, that is, 3.3 N/5 mm or more, the tube 10 and the bag body 20 may adhere to one another. Further, if the peel strength of the welded part is 30 N/15 mm, that is, 10 N/5 mm or more, or the welded part is not delaminated but the film is fractured during peeling test, the tube 10 and the bag body 20 may be firmly welded to each other.

The peel strength is measured based on JIS Z 0238. Specifically, the above peel strength is the peel strength at 90° to be measured under conditions of a temperature of 23±2° C., a relative humidity of 50±5% and a peeling speed of 300 mm/min.

Since the tube 10 and the bag body 20 have excellent heat resistance, it is possible to sufficiently withstand high pressure steam sterilization after filling the infusion bag 100 with the medical infusion.

Figure 3:
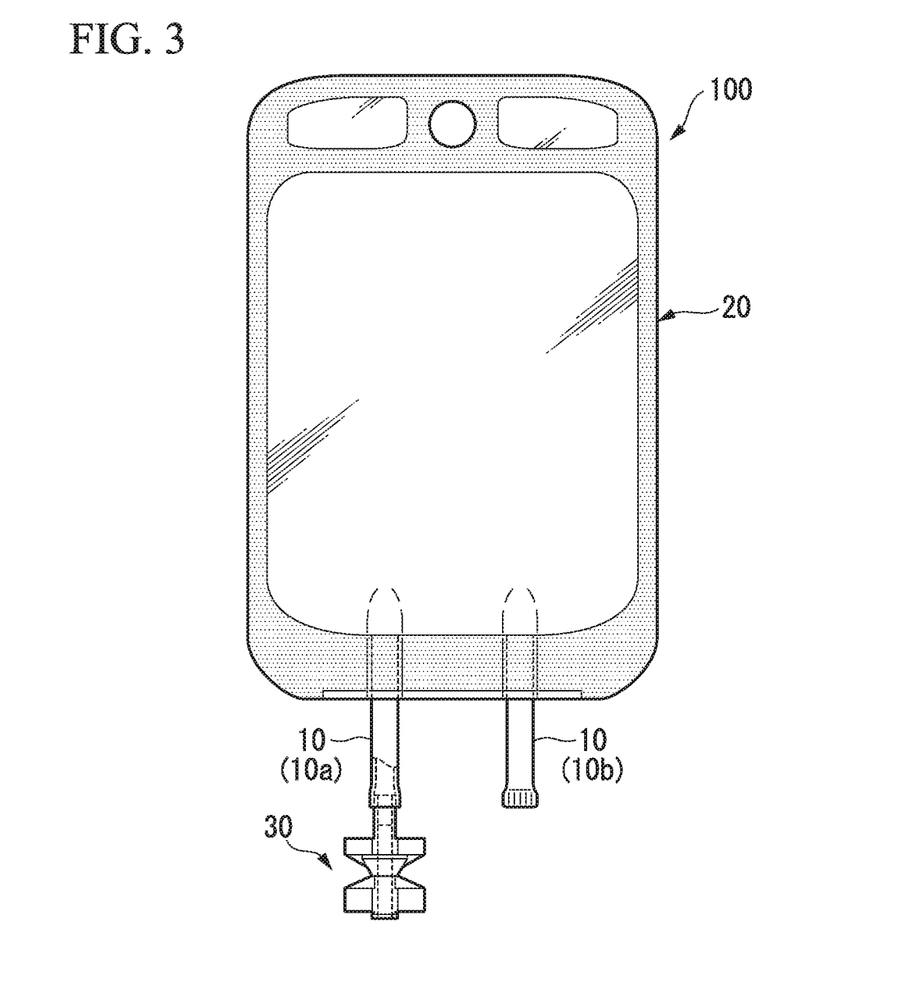
FIG. 3 is a front view illustrating an embodiment of a tube of the medical infusion bag for medical use shown in FIG. 2, to which a connector is attached.

After filling the infusion bag with the medical infusion, for instance, as shown in FIG. 3, the connector 30 is put in one tube 10a of two tubes 10 and plugged, while the other tube 10b is deflated by heat sealing to be plugged, and then subjected to high pressure steam sterilization.

When the tube of the present invention is used, the tube can be firmly adhered by heat during high pressure steam sterilization, even using a simple plug, to such an extent that the connector cannot be separated from the tube again. Therefore, it is not required to weld the tube to the connector by heat sealing before high pressure steam sterilization. However, if stronger sealing is demanded, a close contact part between a plug and the tube may be heat sealed using, for example, a mold, after plugging. As a result, adhesion between the tube and the connector can be further improved.

Instead of heat sealing the front end of the other tube 10b, the tube may be plugged by inserting the connector therein.

A port commercially available from the market such as a twist-off spike port can be used as the connector 30.

The connector 30 is generally made of polypropylene and has excellent heat resistance. Therefore, it is possible to withstand high pressure steam sterilization.

With respect to the tube 10 of the present invention, the connector 30 and an inner layer of the tube 10 contacting the connector 30 include the same propylene-based material. Therefore, adhesion between the tube 10 and the connector 30 is also excellent.

EXAMPLE

Hereinafter, the present invention will be described in detail by illustrating examples and comparative examples. However, the present invention is not limited to the following description.

Assessment methods executed in respective examples and comparative examples are shown as follows:

[Assessment]

(1) Assessment of Transparency

Transparency of the tube was assessed by the following procedure.

Polyethylene films having haze of about 60% and 30% were prepared beforehand. A tube cut after high pressure steam sterilization was compared to the preliminarily prepared polyethylene film by eye and results thereof were assessed according to the following standards.

Transparency: More transparent than the polyethylene film having haze of 30%.

Semi-transparency: More opaque than the polyethylene film having haze of 30% but more transparent than the polyethylene film having haze of 60%.

Opacity: More opaque than the polyethylene film having haze of 60%.

(2) Assessment of Heat Resistance

To assess heat resistance of the tube, an external appearance of the tube after high pressure steam sterilization was observed by eye and results thereof were assessed according to the following standards.

Good: A surface of the tube is smooth and even, the tube is not deformed or detached from the bag body, and/or the connector is not detached from the tube Bad: Unevenness or crimping occurs on the surface of the tube and deformation of the tube is found.

(3) Assessment of Adhesiveness

Assessment 1: Assessment of Adhesion Between the Bag Body and the Tube

Peel strength at a part welded between the film of the bag body and the tube was measured.

Specifically, after heat pressure steam sterilization, the welded part between the bag body and the tube was cut into strips having a width of 5 mm in a width direction of the bag, and subjected to a peeling test based on JIS Z 0238 under conditions of a temperature of 23±2° C., a relative humidity of 50±5% and a peeling speed of 300 mm/min, followed by measurement of a peel strength at 90°.

In addition, conditions of the bag body and the tube after the peeling test were visually observed. When the film is fractured, it is referred to as "film fracture," and when the welded part is peeled off, it is referred to as "delamination." "Film fracture" indicates a higher peel strength than "delamination."

Assessment 2: Assessment of Adhesion Between the Tube and the Connector.

After putting the connector into the tube so as to closely contact to inner surface thereof and executing high pressure steam sterilization, a shape of the tube when the connector was twisted and removed from the tube and a shape of the peeled face at the connector side after cutting off the tube together with the connector and delamination of the part adhered between the connector and the tube were observed, and assessed according to the following assessment standards.

A: The connector cannot be removed from the tube. Delamination occurs through cohesive failure and the tube piece was observed above the peeling face.

B: The connector cannot be removed from the tube. Delamination occurs through interface delamination and the peeling face was smooth.

C: The connector can be removed from the tube.

(4) Assessment of Flexibility

Flexibility of the tube was assessed in two stage of "flexible" and "stiff" based on the touch of the tube when the tube was bent by hand after high pressure steam sterilization.

[Types of Resin]

In respective examples and comparative examples, physical properties of the resin used in fabricating the tube are shown in Table 1.

In addition, a melt flow rate (MFR) was measured based on JIS K7210, in particular, at 190° C. for polyethylene and at 230° C. for other resins under a load of 21.18 N.

A density was measured based on JIS K 7112 D method. Mw/Mn was measured by gel permeation chromatography and calculated in terms of polystyrene.

TABLE 1

| | Resin name | MFR [g/10 min] | Density [g/cm³] | Mw/Mn | Ethylene Content [Mass %] | Content of ethylene/propylene elastomer [Mass %] |
|---|---|---|---|---|---|---|
| Resin material for outer layer | HDPE1 | 0.6 | 0.956 | 4.3 | — | — |
| | HDPE2 | 5.0 | 0.953 | 5.9 | — | — |
| | HDPE3 | 3.5 | 0.950 | 8.2 | — | — |
| | LLDPE | 0.8 | 0.940 | 5.5 | — | — |
| Resin material for inner layer | Random PP1 | 0.6 | 0.89 | — | 8 | — |
| | Random PP2 | 2.3 | 0.90 | — | 2 | — |
| | Block PP1 | 2.8 | 0.89 | — | — | 45 |
| | Block PP2 | 1.7 | 0.89 | — | — | 10 |
| Adhesive resin | PP elastomer blend | 2.7 | 0.89 | — | — | — |
| | Acid-modified polypropylene | 3.5 | 0.88 | — | — | — |
| | Block copolymer | 2.5 | 0.88 | — | — | — |

In Table 1, "HDPE" represents high density polyethylene, "LLDPE" represents linear low-density polyethylene, and "PP" is polypropylene.

Further, a "PP elastomer blend" is a mixture of 60 mass % of block PP1, 20 mass % of an olefin-based elastomer of an ethylene-butene copolymer and 20 mass % of a styrene-based elastomer. "Acid-modified polypropylene" is maleic acid anhydride-modified polypropylene ("ZELAS MC721AP" manufactured by Mitsubishi Chemical Co. Ltd.). "Block copolymer" is block copolymer having a structure of ethylene chain-ethylene/butylene chain-ethylene chain ("DYNARON 6200P" manufactured by JSR Co. Ltd.).

Example 1

Fabrication of Tube

As shown in Table 2, HDPE1, block PP1 and a PP elastomer blend were used for an outer layer, an inner layer and an adhesive layer, respectively. The outer layer, adhesive layer and inner layer were sequentially laminated into three layers to form a tube having an outer diameter of 8 mm and inner diameter of 6 mm by means of a multi-layer tube molding machine (manufactured by PLAGIKEN Co., Ltd.). As a result of measuring a thickness of each layer, it was determined that the outer layer, adhesive layer and inner layer had thicknesses of 20 μm, 10 μm and 970 μm, respectively. In addition, a thickness of the tube wall was 1 mm.

<Production of Medical Infusion Bag>

First, the outer layer was prepared using a mixture of low-density polyethylene (density: 0.928 g/cm³) and high-density polyethylene (density: 0.956 g/cm³) in a ratio of 7:3. Similarly, the intermediate layer was prepared using a mixture of linear low-density polyethylene (density: 0.908 g/cm³) and high-density polyethylene (density: 0.956 g/cm³) in a ratio of 8:2 while the inner layer was prepared using high-density polyethylene (density: 0.956 g/cm³). The prepared outer layer, intermediate layer and inner layer were sequentially laminated to form a three-layer polyethylene film by means of a water cooling type co-extrusion multi-layer inflation molding machine. As a result of measuring a thickness of each layer, it was determined that the outer layer, intermediate layer and inner layer had thicknesses of 25 μm, 215 μm and 25 μm, respectively. Predetermined sites of the obtained polyethylene film were heat sealed to become a back shape, and thereby a bag body was obtained.

Next, two tubes were welded by heat sealing to the bottom of the prepared bag body, so as to produce an infusion bag shown in FIG. 2.

After introducing purified water into the bag body through the tube, a twist-off spike port made of polypropylene (manufactured by Marudi Co. Ltd.) as a connector was put in a front end of the tube and then plugged. This was subjected to high pressure steam sterilization under the condition of 121° C.×30 minutes.

After high pressure steam sterilization, the treated tube was assessed in terms of transparency, heat resistance, adhesion between the bag body and the tube, adhesion between the tube and the connector, and flexibility. Assessed results are shown in Table 3.

Examples 2 to 9

The same procedures as described in Example 1 were carried out except that types of resins to construct the outer layer, inner layer and adhesive layer were changed as shown in Table 2, so as to prepare a tube including the outer layer, adhesive layer and inner layer sequentially laminated therein. An infusion bag was produced using the prepared tube and subjected to the assessments described above. Assessed results are shown in Table 3.

Alternatively, in Example 4, the inner layer of the tube had a double-layer structure that included a layer made of block PP1 on the outer layer side (with a thickness of 960 μm) and a layer made of a PP elastomer blend on the liquid contact side (with a thickness of 10 μm).

Example 10

The same procedures as described in Example 1 were carried out except that a resin used for forming the outer layer was a mixture of HDPE1 and a block copolymer in a ratio of 50:50 and no adhesive layer was provided between the outer layer and the inner layer, so as to prepare a double-layer type tube having a laminate of the outer layer and inner layer. An infusion bag was produced using the prepared tube and subjected to the assessments described above. Assessed results are shown in Table 3.

Example 11

An infusion bag was produced according to the procedures as described in Example 1, except that a twist-off spike port made of polycarbonate was used as a connector, and then subjected to the assessments described above. Assessed results are shown in Table 3.

Example 12

An infusion bag was produced according to the procedures as described in Example 1, except that the same tube as that used in Example 4 and a twist-off spike port made of polycarbonate, as a connector, were used, and then subjected to the assessments described above. Assessed results are shown in Table 3.

Comparative Example 1

The block polypropylene used herein was block PP1 and a mono-layer tube having a thickness of 1 mm was prepared by means of a multi-layer tube molding machine (manufactured by PLAGIKEN Co. Ltd.).

An infusion bag was produced according to the procedures as described in Example 1, except that the above prepared tube was used, and then subjected to the assessments described above. Assessed results are shown in Table 3.

Comparative Example 2

The same procedures as described in Example 1 were carried out except that LLDPE was used as the resin material for the outer layer to form the outer layer, so as to prepare a tube including the outer layer, adhesive layer and inner layer sequentially laminated therein. An infusion bag was produced using the prepared tube and subjected to the assessments described above. Assessed results are shown in Table 3.

Comparative Example 3

The same procedures as described in Example 1 were carried out except that LLDPE was used as the resin material for the outer layer to form the outer layer, so as to prepare a tube including the outer layer, adhesive layer and inner layer sequentially laminated therein. An infusion bag was produced according to the procedures as described in Example 1, except that the prepared tube was used and a sterilization temperature was changed to 115° C., and then subjected to the assessments described above. Assessed results are shown in Table 3.

TABLE 2

| | Configuration of tube | | | Thickness [μm] | | |
|---|---|---|---|---|---|---|
| | Outer layer | Adhesive layer | Inner layer | Outer layer | Adhesive layer | Inner layer |
| Example 1 | HDPE1 | PP elastomer blend | Block PP1 | 20 | 10 | 970 |
| Example 2 | HDPE2 | PP elastomer blend | Block PP1 | 20 | 10 | 970 |
| Example 3 | HDPE3 | PP elastomer blend | Block PP1 | 20 | 10 | 970 |
| Example 4 | HDPE1 | PP elastomer blend | Block PP1    PP elastomer blend | 20 | 10 | 960   10 |
| Example 5 | HDPE1 | PP elastomer blend | Random PP1 | 20 | 10 | 970 |
| Example 6 | HDPE1 | PP elastomer blend | Random PP2 | 20 | 10 | 970 |
| Example 7 | HDPE1 | PP elastomer blend | Block PP2 | 20 | 10 | 970 |
| Example 8 | HDPE1 | Acid-modified polypropylene | Block PP1 | 20 | 10 | 970 |
| Example 9 | HDPE1 | Block copolymer | Block PP1 | 20 | 10 | 970 |
| Example 10 | Blend of HDPE1 and block copolymer | — | Block PP1 | 30 | — | 970 |
| Example 11 | HDPE1 | PP elastomer blend | Block PP1 | 20 | 10 | 970 |
| Example 12 | HDPE1 | PP elastomer blend | Block PP1    PP elastomer blend | 20 | 10 | 960   10 |
| Comparative Example 1 | | Block PP1 | | | 1000 | |
| Comparative Example 2 | LLDPE | PP elastomer blend | Block PP1 | 20 | 10 | 970 |
| Comparative Example 3 | LLDPE | PP elastomer blend | Block PP1 | 20 | 10 | 970 |

TABLE 3

| | | | | Adhesiveness | | | |
|---|---|---|---|---|---|---|---|
| | | | | Assessment 1 | | | |
| | Sterilization temperature [° C.] | Transparency | Heat resistance | Condition after peeling test | Peel strength [N/5 mm] | Assessment 2 | Flexibility |
| Example 1 | 121 | Transparent | Good | Film fracture | 27 | A | Flexible |
| Example 2 | 121 | Transparent | Good | Film fracture | 27 | A | Flexible |

TABLE 3-continued

|  | Sterilization temperature [° C.] | Transparency | Heat resistance | Adhesiveness Assessment 1 Condition after peeling test | Peel strength [N/5 mm] | Assessment 2 | Flexibility |
|---|---|---|---|---|---|---|---|
| Example 3 | 121 | Semi-Transparent | Good | Film fracture | 26 | A | Flexible |
| Example 4 | 121 | Transparent | Good | Film fracture | 27 | A | Flexible |
| Example 5 | 121 | Transparent | Good | Film fracture | 27 | A | Flexible |
| Example 6 | 121 | Transparent | Good | Film fracture | 28 | B | Stiff |
| Example 7 | 121 | Transparent | Good | Film fracture | 28 | B | Stiff |
| Example 8 | 121 | Transparent | Good | Film fracture | 27 | A | Flexible |
| Example 9 | 121 | Transparent | Good | Film fracture | 25 | A | Flexible |
| Example 10 | 121 | Transparent | Good | Film fracture | 26 | A | Flexible |
| Example 11 | 121 | Transparent | Good | Film fracture | 26 | B | Flexible |
| Example 12 | 121 | Transparent | Good | Film fracture | 26 | A | Flexible |
| Comparative Example 1 | 121 | Transparent | Good | Delimitation | 9 | A | Flexible |
| Comparative Example 2 | 121 | Opaque | Bad | Film fracture | 26 | A | Flexible |
| Comparative Example 3 | 115 | Transparent | Good | Film fracture | 28 | C | Flexible |

As clearly shown in Table 1, it can be seen that the tube prepared in each of the examples is transparent or semi-transparent even after high pressure steam sterilization at 121° C., and therefore it is possible to maintain transparency.

The infusion bag having each of the tubes has sufficient peel strength at the welded part between the bag body and the tube even after high pressure steam sterilization at 121° C., and the tube is firmly adhered to the bag body made of polyethylene. In addition, the tube was not deformed and did not detach from the bag body, and/or the connector did not detach from the tube.

In addition, the tube prepared in Comparative Example 1 is still transparent even after high pressure steam sterilization at 121° C., and thereby it is possible to maintain transparency. Further, the infusion bag having this tube is not deformed even after high pressure steam sterilization at 121° C. In addition, the tube did not detach from the bag body and/or the connector did not detach from the tube.

However, the infusion bag in Comparative Example 1 has a low peel strength of 9 N/5 mm at the welded part between the bag body and the tube and insufficient adhesiveness.

The infusion bag having the tube prepared in Comparative Example 2 has substantially the same peel strength at the welded part between the bag body and the tube as the infusion bag produced in each of the above examples, even after high pressure steam sterilization at 121° C. Further, the connecter did not detach from the tube.

However, in the case of the infusion bag in Comparative Example 2, the tube was deformed when it was subjected to high pressure steam sterilization at 121° C. In contrast, it is found that a tube having an outer layer made of linear low-density polyethylene shows lower heat resistance than the above tube. In addition, the tube became opaque after high pressure steam sterilization.

The tube prepared in Comparative Example 3 is still transparent even after sterilization at 115° C., and maintains transparency. Further, the infusion bag having this tube maintains substantially the same peel strength at the welded part between the bag body and the tube as the infusion bag produced in each of the above examples, even after sterilization at 115° C. Meanwhile, in Comparative Example 3, since a sterilization temperature is relatively low such as about 115° C., the tube can maintain heat resistance at this temperature.

However, for the infusion bag in Comparative Example 3, the connector is easily detached from the tube and adhesion between the tube and the connector is insufficient.

INDUSTRIAL APPLICABILITY

According to the present invention, a multi-layer tube for medical use, which has excellent heat resistance and adhesiveness to both of a polyethylene bag and a connector, as well as a medical infusion bag including the multi-layer tube for medical use, may be provided.

DESCRIPTION OF REFERENCE NUMERALS

10: multi-layer tube for medical use
11: outer layer
12: inner layer
13: adhesive layer
20: bag body
30: connector
100: medical infusion bag

The invention claimed is:
1. A multi-layer tube for medical use which is used as a tube port and is welded to a bag body of a medical infusion bag through which the medical infusion is discharged from the bag body, comprising:

an outer layer which is welded to an inner layer of the medical infusion bag by heat, the outer layer consists of 100 mass % of a high-density polyethylene;

an inner layer comprising a polypropylene resin material that contains random polypropylene and/or block polypropylene; and an adhesive layer that adheres the high-density polyethylene of the outer layer and the polypropylene resin material of the inner layer which is provided between the outer layer and the inner layer, wherein the inner layer of the medical infusion bag comprising a resin material that consists of polyethylene, wherein a density of the high-density polyethylene is $0.945$ g/cm$^3$ or more.

2. A medical infusion bag comprising the multi-layer tube according to claim 1 and a bag body made of a polyethylene film in a bag-form, which stores a medical infusion, and a tube port welded to a bottom of the bag body, through which the medical infusion is discharged from the bag body.

3. The medical infusion bag according to claim 2 comprised of the polyethylene film of a multi-layer structure, wherein an inner layer of the medical infusion bag contains a high-density polyethylene.

\* \* \* \* \*